(12) United States Patent
Nishimura et al.

(10) Patent No.: US 7,598,372 B2
(45) Date of Patent: Oct. 6, 2009

(54) SYNTHESIS OF CORE SUGAR CHAIN STRUCTURE OF ASPARAGINE-LINKED GLYCOPROTEIN

(75) Inventors: Shinichiro Nishimura, Sapporo (JP); Yasuhiro Takegawa, Sapporo (JP)

(73) Assignee: Shionogi & Co., Ltd., Osaka (JP)

( * ) Notice: Subject to any disclaimer, the term of this patent is extended or adjusted under 35 U.S.C. 154(b) by 46 days.

(21) Appl. No.: 10/584,065

(22) PCT Filed: Dec. 24, 2004

(86) PCT No.: PCT/JP2004/019384
§ 371 (c)(1),
(2), (4) Date: Jun. 22, 2006

(87) PCT Pub. No.: WO2005/063782
PCT Pub. Date: Jul. 14, 2005

(65) Prior Publication Data
US 2007/0166783 A1 Jul. 19, 2007

(30) Foreign Application Priority Data
Dec. 26, 2003 (JP) .............................. 2003-433717

(51) Int. Cl.
C08B 37/00 (2006.01)
C07H 5/04 (2006.01)
C07H 5/06 (2006.01)

(52) U.S. Cl. ..................... 536/55.3; 536/29.1

(58) Field of Classification Search ................ None
See application file for complete search history.

(56) References Cited

FOREIGN PATENT DOCUMENTS

JP 2001-524484 12/2001
WO 99-26956 6/1999

OTHER PUBLICATIONS

Usui et al. Glycoconjugate Journal (1994) 11: 105-110.*
Yamazaki et al. Holzoforschung (1979), 33(2), 36-42.*
Takatani et al. Glycoconjugate Journal 17, 361-375, 2000.*
Greene et al. Protective Groups in Organic Synthesis, Third Edition, 1999 John Wiley & Sons, Reactivity Chart 1, pp. 708-711.*
D. N. Bolam et al., "Synthesis of 2,4-Dinitrophenyl Glycosides of D-Xylobiose and D-Mannobiose", Carbohydrate Research, vol. 312, pp. 85-89, 1998.
W. Gunther et al., "Synthesis of a β-Mannosyl-Chitobiosyl-Asparagine Conjugate—A Central Core Region Unit of the N-Glycoproteins", Angew. Chem. Int. Ed. Engl., vol. 29, No. 9, pp. 1050-1051, 1990. (English version of Angewandte Chemie, vol. 102, No. 9, pp. 1068-1069, 1990).
H. Kunz et al., "β-Mannosides from β-Glucosides by Intramolecular Nucleophilic Substitution with Inversion of Configuration", Angew. Chem. Int. Ed. Engl., vol. 27, No. 8, pp. 1086-1087, 1988.

* cited by examiner

Primary Examiner—Shaojia Anna Jiang
Assistant Examiner—Layla Bland
(74) Attorney, Agent, or Firm—Wenderoth, Lind & Ponack, L.L.P.

(57) ABSTRACT

It is intended to chemically synthesize the trisaccharide moiety at the reducing end in the core sugar chain structure of an asparagine-linked glycoprotein. By using a highly inexpensive natural polysaccharide having a mannoseβ-1,4-bond as the starting material, a β-1,4-glycoside bond of mannose is formed.

9 Claims, No Drawings

SYNTHESIS OF CORE SUGAR CHAIN STRUCTURE OF ASPARAGINE-LINKED GLYCOPROTEIN

TECHNICAL FIELD

The present invention relates to a field of chemical synthesis of sugar chain, and specifically, to a convenient method for chemically synthesizing sugar chains of glycoprotein and a synthetic intermediate thereof.

BACKGROUND ART

Glycoprotein means a protein comprising a moiety of oligosaccharide referred to as a sugar chain.

Recently, glycoprotein has been found to be closely involved with biological processes such as cell adhesion or signaling, and structures of sugar chains which trigger various biological processes have gradually emerged. However, only a small amount of glycoprotein is expressed in a living body for the sugar chain to mediate a biological process, and it is quite difficult to obtain pure glycoprotein in sufficient quantity to determine the chemical and physical properties of the sugar chain.

An asparagine-linked glycoprotein is one of the glycoproteins and ubiquitously found in human serum or ovalbumin. The asparagine-linked glycoprotein is classified into a high mannose-type, a complex type and a mixed type according to characteristics of a branch of the sugar chain and/or constituting sugar. All of these types have a common core sugar chain structure of a penta-saccharide comprising three molecules of mannose and two molecules of N-acetyl glycosamine at the reducing terminal of the chain;

not yet known. One of the reasons is that the core sugar chain structure contains a moiety chemical synthesis of which is quite difficult.

In the chemical synthesis of the core sugar chain structure, it is extremely difficult to form a bond of mannoseβ-glycoside, that is a bond of β-manno-glycoside (Manβ1→4-GlcNAc). The reason comes from the facts that a neighboring group effect is not available since 2-OH group of mannose is linked at the axial position and the β-manno glycoside bond brought an electrically unstable structure against an anomer effect typically found in sugars. Kunz et al. discloses a chemical method for preparing a β-manno glycoside structure, which contains a complicated process and requires the time and cost of running (Kunz, H. and Gunther, W. (1988) Angew. Chem. Int. Ed. Engl. 27, 1086-1087).

Other reasons why a bond of β-manno glycoside (Manβ1→4-GlcNAc) is difficult to be formed are that the acceptor of the glycosilation reaction is N-acetyl glucosamine of low solubility in the reaction medium and the reactivity of 4-OH group is low compared with the other OH groups (reactivities of OH groups; 1-OH>>6-OH>>2-OH>3-OH>4-OH).

In addition, synthesis of a structure of GlcNAcβ1→4GlcNAc has some problems in the chemical synthesis of the core sugar chain structure of asparagine-linked sugar chain.

As described above, synthesis of the trisaccharide (Manβ1→4GlcNAcβ1→4GlcNAc) at the reducing terminal especially remains as a big problem in the chemical synthesis of the core sugar chain structure of asparagine-linked sugar chain. In order to synthesize the core sugar chain structure,

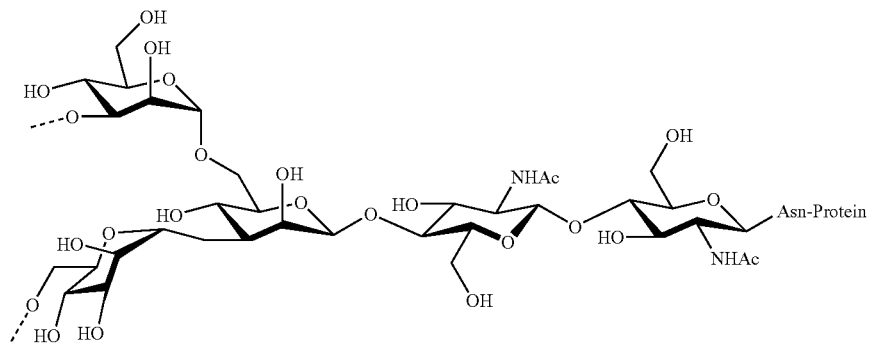

the core sugar chain structure of asparagine-linked glycoprotein

Accordingly, chemical synthesis of the core sugar chain structure shown in the formula above provides the basis for studying the function of asparagine-linked sugar chain.

DISCLOSURE OF INVENTION

However, an efficient method for synthesizing the core sugar chain structure of the asparagine-linked sugar chain is how to synthesize the β-manno glycoside bond effectively is especially an issue to be solved.

The inventors of the present invention focused their attention to a natural polysaccharide having the structure of mannosideβ1→4 bonds, especially galactomannan, guar gum and mannan, which have mannosideβ1→4 bonds.

The objective of the present invention is to break the primary barrier in the synthesis of the core sugar chain structure, specifically to form a β-manno-glycoside bond by using a disaccharide unit of Manβ1→4Man comprised in a structure of natural polysaccharides, and to establish an efficient method for synthesizing the structure of the core sugar chain.

As a result, the present invention relates to a method comprising, (1) a process of preparing a compound of mannose disaccharide (a type of ManP$^1$β1→4ManP$^1$) shown with a formula (I);

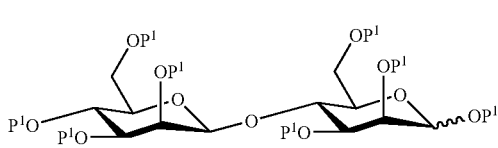
(I)

wherein P$^1$ is an OH-protecting group and the wavy line means that —OP$^1$ is linked at an axial or equatorial position or mixture of both, by hydrolyzing a polysaccharide having mannoseβ-1,4-bonds, preferably galactomannan, guar gum or mannan having mannoseβ-1,4-bonds, more preferably a galactomannan derivative shown with a formula (V);

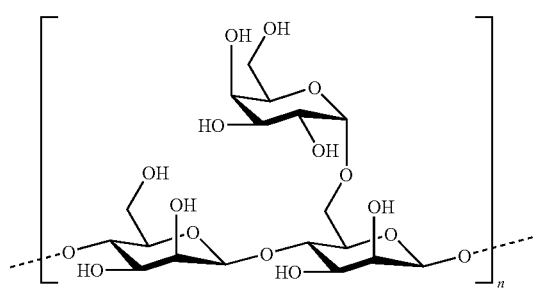
(V)

(n is an integer of 50 or more)

or a mannan derivative shown with a formula (VI);

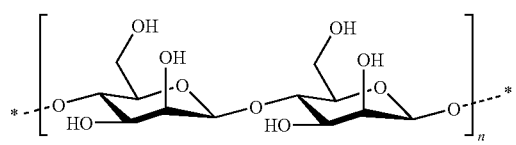
(VI)

(n is an integer of 50 or more)

and protecting hydroxyl groups of the resulted compound, (2) each process for converting the obtained mannose disaccharide compound (a type of ManP$^1$β1→4ManP$^1$) into a glycal compound in which mannose at the reducing terminal of the mannose disaccharide compound is changed into a glycal, by halogenating and reducing the mannose disaccharide, and (3) preparing an azide disaccharide compound (a type of ManP$^1$β1→4ManP$^1$) shown with a formula (II) in which the 2-azide group of mannose in the reducing terminal is linked at the equatorial position;

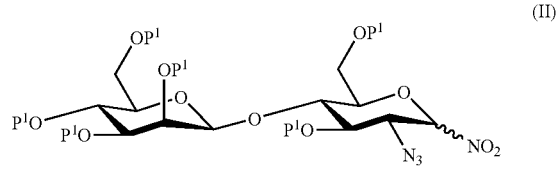
(II)

wherein P$^1$ is the same above, and the wavy line means that —NO$_2$ is linked at an axial or equatorial position or mixture of both, by azidenitration reaction of the glycal compound above, (4) each process for substituting the nitro group of the azide disaccharide compound (a type of ManP$^1$β1→4ManP$^1$) with a leaving group, preferably (4-1) substituting the nitro group of the azide disaccharide compound (a type of ManP$^1$β1→4ManP$^1$) with a —OP$^{10}$ group (P$^{10}$ is an OH-protecting group), and preparing a trihaloacetoimidate derivative by reacting with trihaloacetonitrile after removal of the P$^{10}$ group, or (4-2) substituting the nitro group of the azide disaccharide compound (a type of ManP$^1$β1→4ManP$^1$) with a leaving group, and (5) preparing a trisaccharide compound (a type of Manβ1→4GlcNP$^1$β1→4GlcNP$^2$) shown with a formula (III);

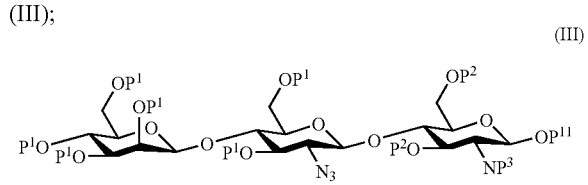
(III)

wherein P$^1$, P$^2$, P$^3$ and P$^{11}$ are the same above, by reacting the derivative above in which a leaving group was introduced with amino-protected glucopyranoside of the formula

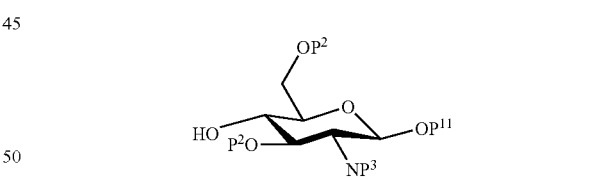

wherein P$^2$ and P$^{11}$ are an OH-protecting group and P$^3$ is an amino-protecting group, and (6) a process for preparing an asparagine-linked trisaccharide compound (Manβ1→4GlcNP$^1$β1→4GlcNP$^2$) shown with a formula (IV);

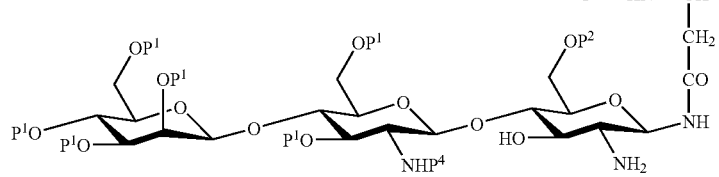
(IV)

wherein $P^1$ and $P^2$ are the same above, $P^4$ and $P^6$ are independently amino protecting groups and $P^5$ is a carboxyl-protecting group, and a method of each process, when preparing the trisaccharide (Manβ1→4GlcNβ1→4GlcN) at the reducing terminal of the core sugar chain structure in the asparagine-linked glycoprotein.

Furthermore, the present invention relates to the azide disaccharide compound (a type of ManP$^1$β1→4ManP$^1$) of the formula (II) which is a useful synthetic intermediate in the methods of the present invention;

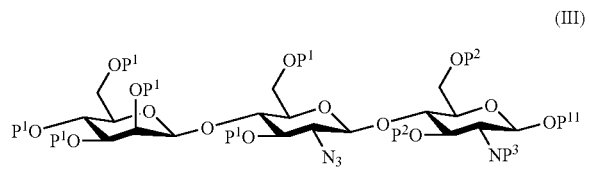

(II)

wherein $P^1$ is an OH-protecting group, the wavy line means that —NO$_2$ is linked at an axial or equatorial position or mixture of both, and to the trisaccharide compound shown with the formula (III);

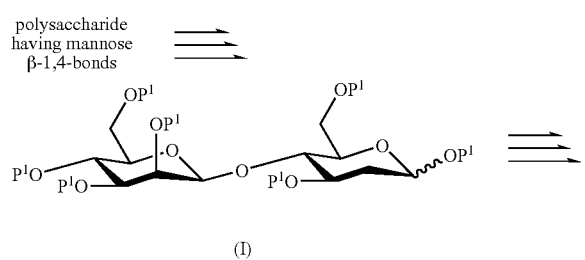

(III)

wherein $P^1$, $P^2$ and $P^{11}$ are OH-protecting groups and $P^3$ is an amino-protecting group.

According to the present invention, the trisaccharide moiety (Manβ1→4GlcNβ1→4GlcN) of the reducing terminal in the core sugar chain structure of the asparagine-linked glycoprotein sugar chain is easily synthesized and it is useful to clarify the function and structure-characteristics of the asparagine-linked glycoprotein which causes various life processes.

BEST MODE FOR CARRYING OUT THE INVENTION

The outline of the novel route for synthesizing the core sugar chain structure in the present invention is depicted as follows;

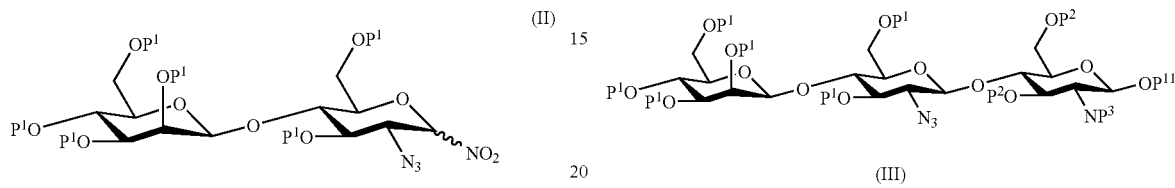

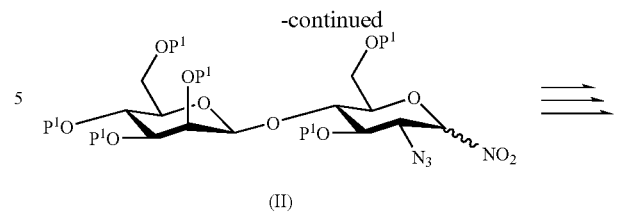

(II)

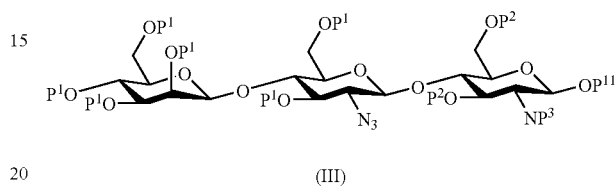

(III)

wherein the wavy line means that the —OP$^1$ or nitro group is linked at an axial or equatorial position or mixture of both.

At first, the disaccharide compound (I), Manβ1→4Man, is obtained after acid hydrolysis of a polysaccharide having mannose β-1,4-bonds and acetylation of the product. Next, it is converted to the glycal derivative wherein mannose of the reducing terminal was converted to glycal by a chemical method, and followed by azide nitration reaction to give the compound (II). The compound (II) which has the equatorial 2-azide group at the reducing terminal can be transformed to the moiety of Manβ1→4GlcNAc in the core sugar chain structure and is a useful key intermediate.

Thus, the intermediate (II) is easily converted to the moiety of Manβ1→4GlcNAc which is difficult to prepare through other synthetic scheme, while the intermediate (II) can be easily prepared in a large scale at a reasonable cost from the compound (I), which is available from galactomannan, guar gum or mannan derivatives. Furthermore, the trisaccharide compound (III), which is ready to be converted to the trisaccharide (Manβ1→4GlcNAcβ1→4GlcNAc) of the reducing terminal in the core sugar chain structure, is synthesized when the intermediate (II) is used as a glycosyl donor.

Thus, the inventors of the present invention succeeded to simplify the scheme for synthesizing the trisaccharide of the reducing terminal in the core structure by utilizing a natural polysaccharide available at a low cost.

In the following description, each process of the present invention is explained in detail.

Process (1)

In Process (1), the compound (I) of mannose disaccharide (ManP$^1$β1→4ManP$^1$) is prepared from a polysaccharide having mannoseβ-1,4-bonds. At first, a polysaccharide having mannoseβ-1,4-bonds is hydrolyzed, the OH groups are protected and the desired disaccharide is isolated.

As a starting material, a polysaccharide having mannoseβ-1,4-bonds, preferably galactomannan, guar gum or mannan having mannoseβ-1,4-bonds, more preferably a galactomannan derivative of the formula (V);

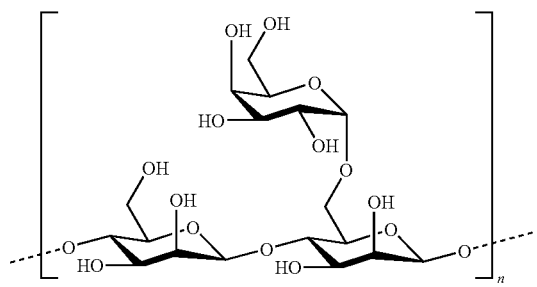

(V)

wherein n is an integer of 50 or more or a mannan derivative of the formula (VI);

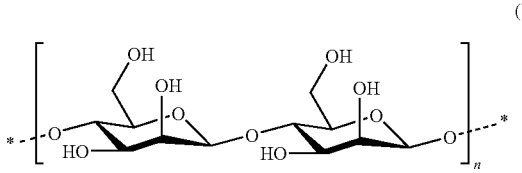

(VI)

wherein n is an integer of 50 or more is used.

Galactomannan derivatives (also referred to as galactomannoglycan) are extensively present in seeds of legume family, e.g., alfalfa or clover. Galactomannan in the seeds of guar (*Cyamopsis tetragonolobus*) and carob or locust bean (*Ceratonia siliqua*) is available in the market as gum products derived from plants.

Guar gum extracted from guar seeds is a natural polysaccharide having a straight sugar chain comprising a series of mannose β1→4 bonds wherein galactose is linked through α1→6 bond to every mannose residue as a branch. Almost uses of this material are food additives such as thickeners of various canned products, quality improving agent (inhibitor of shape-loosing) or taste-regulator of various foods and easily available at an extremely low cost.

A mannan derivative is a generic name of polysaccharides comprised of D-mannose. Plant mannan derivatives contained in endosperm of ivory nut or bulbs of orchidaceous plant have straight chain structure in which D-mannose residues are linked through β1→4 bonds and insoluble in water.

In detail, these are described in "Comprehensive Dictionary for Utilization of Regional Biological Resources", Ed., Hiroshi Fujimaki, 1998, Rural Culture Association; Y. C. Lee, et al. (1977) Analytical Biochem., 79, 329-337; and Shiryo Yaga, et al. (1995) Mokuzai Gakkaishi, vol. 41, No 4, 440-443.

Usually, acid hydrolysis is applied to hydrolyze polysaccharides having mannoseβ-1,4-bonds. For the purpose, sulfuric acid, preferably 10-20% sulfuric acid, trifluoroacetic acid or sulfuric acid-acetic acid is used and the reaction temperature of 50-70° C. is preferable.

Materials of which-the polymerization degree is equal or more than 9 are removed by isolation of galactomannan soluble in 70% EtOH. In general, the polymerization revel is increased the more, the derivative remains in the insoluble residue.

In order to protect the hydroxyl group, acetyl, benzyl, 4-methoxybenzyl, benzoyl, methoxymethyl, tetrahydropiranyl, torimethylsilyl, and triethylsilyl group etc., are usually used.

Isolation of the disaccharide is achieved by silica gel chromatography and/or HPLC.

Process 2

In Process 2, a glycal compound is prepared from the mannose disaccharide compound (I) (a type of ManP$^1$β1→4ManP$^1$). At first, the glycal compound is prepared from the disaccharide by halogenation and successive reduction of the position 1 in mannose of the reducing terminal. Usually, mannose is halogenated around r.t. using hydrogen halide or acid halide etc. Reduction is carried out by using a metal such as zinc etc., while avoiding a reaction at high temperature.

Process 3

In Process 3, the azide disaccharide compound (II), in which the 2-azide group of mannose in the reducing terminal is linked at the equatorial position, is prepared by azidenitration reaction of the glycal compound.

The azidenitration reaction is carried out by simultaneous azidation and nitration. A mixture of equatorial and axial isomers is provided, and the compound having the 2-azide group of mannose in the reducing terminal at the equatorial position is isolated by purifying the mixture.

Process 4

In Process 4 the nitro group in the azide disaccharide compound is substituted for a leaving group, which generally includes fluorine, bromine, chlorine, trichloroacetoimidate, 4-pentenyl, alkylthio (sulfur) and arylthio.

Preferably, the nitro group in the azide disaccharide compound is substituted for the —OP$^{10}$ group (P$^{10}$ is an OH-protecting group), and the trihaloimidate derivative is obtained by the reaction with trihaloacetonitrile after removal of the P$^{10}$ group or a halogenated derivative is obtained by the reaction with hydrogen halide. Alternatively, the —OP$^{10}$ derivative or P$^{10}$-deprotected derivative may be converted to the derivatives having a leaving group such as a penteny, acetylthio or arylthio group.

Process 5

In Process 5, the resulting derivative having a leaving group is reacted with amino-protected glucopyranoside to prepare the trisaccharide compound (a type of Manβ1→4GlcNP$^1$β1→4GlcNP$^2$).

The amino-protected glucopyranoside may be prepared according to the following scheme.

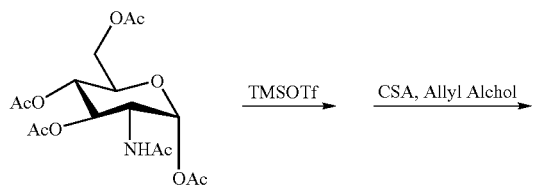

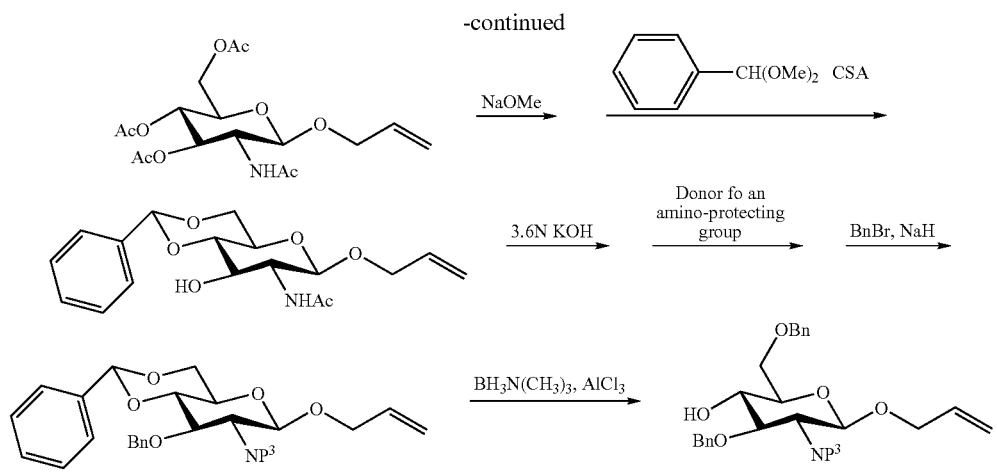

As the P³ group which is an amino protecting group, phthalimide, tert-butyloxycarbonyl, benzyloxycarbonyl, acetyl, benzoyl or benzyl group etc. is usually used.

Next, this compound is reacted with the above derivative having a leaving group under acidic (Lewis-acidic) condition.

Process 6

In Process 6, the trisaccharide compound is coupled with asparagine. The coupling with asparagines is carried out according to the next scheme, for example.

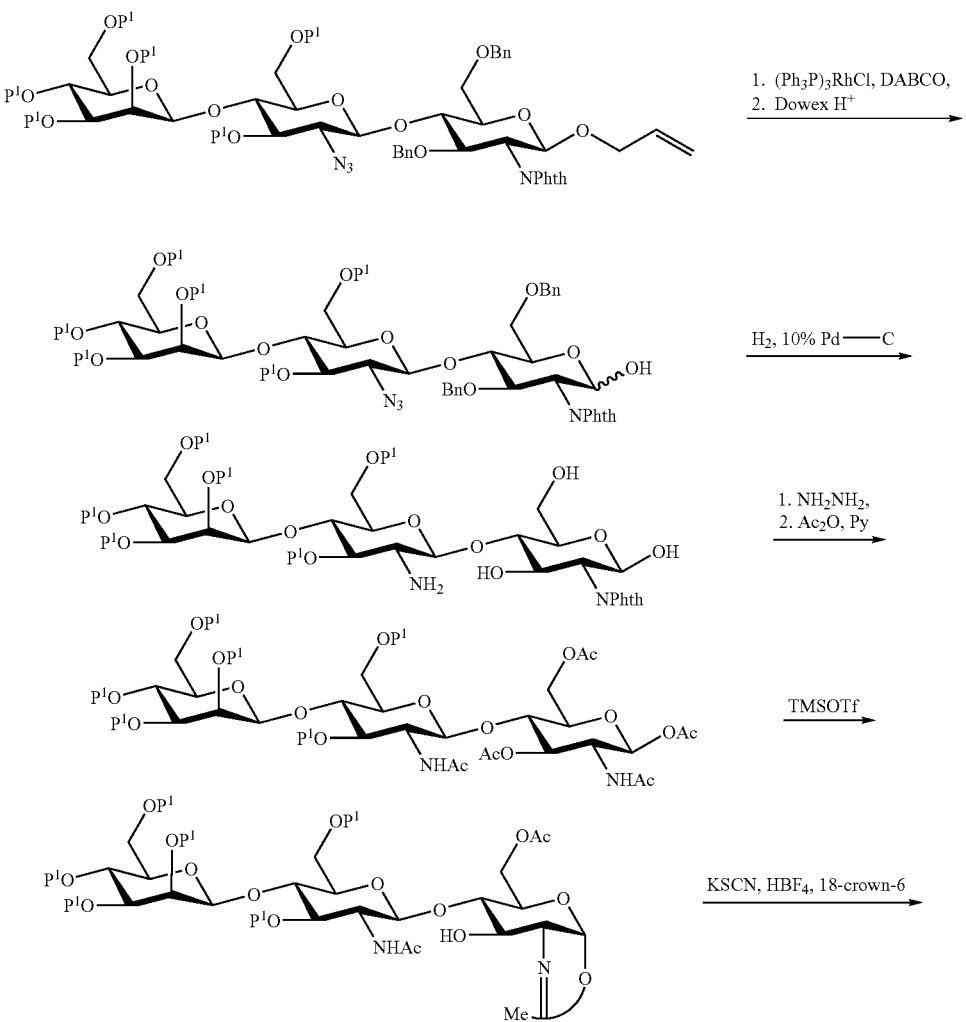

-continued

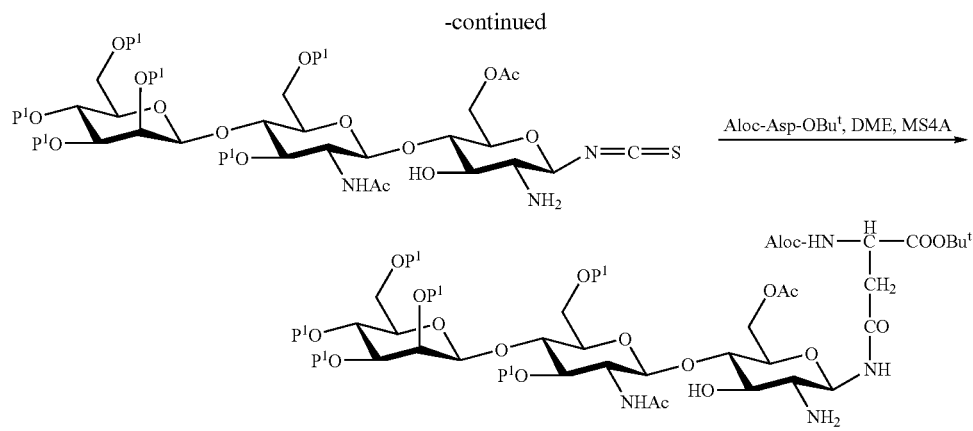

The trisaccharide prepared above may be coupled with an asparagine residue of the desired protein and the sugar chain may be elongated by adding a new sugar unit. Also a pre-elongated sugar chain prepared by adding a sugar unit to the trisaccharide may be introduced to the desired protein.

Alternatively, a protein sequence may be elongated when standard peptide chemistry is applied to the asparagines residue in the asparagines-linked trisaccharide derivative. Also, a sugar chain may be elongated when standard carbohydrate chemistry is applied to mannose in the reducing terminal.

EXAMPLES

The present invention is explained in more detail by the following experiments, but not limited to them.

Materials used in the experiments are obtained from the commercial source described below.

SANSHO Co., Ltd. (Food Division)
   Guargum MEYPROGAT 120S
KANTO CHEMICAL CO., INC
   Zinc Powder
   Copper (II) Sulfate Pentahydrate (crystalline powder)
   Diammonium Cerium (IV) Nitrate
Wako Pure Chemical Industries, Ltd.
   Sodium Acetate
   Acetic Anhydride
   Trifluoroacetic Acid
   Sodium Azide
   DBU, 1,8-Diazabicyclo[5,4,0]undec-7-ene
   $CCl_3CN$, Trichloroacetonitrile
   $BF_3OEt_2$, Boron Trifluoride Diethyl Ether Complex
   Acetic Acid, For Organic Synthesis
   Pyridine, For Organic Synthesis
   Tetrahydrofuran, THF, For Organic Synthesis
   $CH_2Cl_2$, Dichloromethane, For Organic Synthesis
   Acetonitrile, For Organic Synthesis
   Ethyl Acetate
   Chloroform
   Toluene
   Anhydrous $MgSO_4$
   Triethylamine
Tokyo Chemical Industry Co., Ltd.
   30% HBr—AcOH, 30% Hydrogen Bromide in Acetic Acid
Nacalai Tesque, Inc.
   Benzylamine
Japan Alcohol Trading CO., LTD
   99% Ethanol Example 1

1. Hydrolysis of Guar Gum and Isolation of Manβ1→4Man

Synthetic Scheme (1)

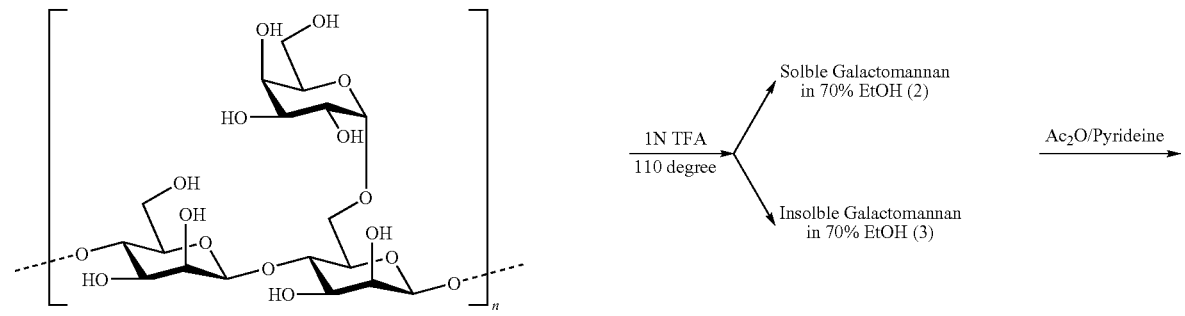

Guargum (1) 200g (large scale)
2.0 g (small scale)

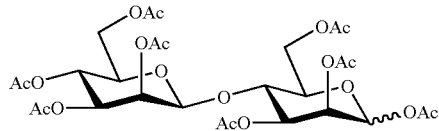

Ac-Mannnobiose (4) 25g (large scale)
0.45g (small scale)

1.1. Hydrolysis of Guar Gum (A Small Scale)

(A) Galactomannan Soluble in 70% EtOH is Obtained by Hydrolysis of Guar Gum with TFA 2.0 g of guar gum (1) was dissolved in 16.6 ml of 1N TFA and heated to 110° C. in an oily bath with stirring for 90 min. The reaction mixture was poured into 40 ml of 99% EtOH and placed at room temperature. The resulting white precipitation was removed by filtration using Buchner funnel and the filtrate was concentrated in vacuo. Toluene was added to the residue and azeotropically distilled several times to give 2.26 g of galactomannan (2) soluble in 70% EtOH and 73 mg of galactomannan (3) insoluble in 70% EtOH.

Analysis of galactomannan (2) soluble in 70% EtOH using MALDI-TOFMS showed that its polymerization degree was reduced to 1-8.

(B) Galactomannan soluble in 70% EtOH is acetylated to give O-(2,3,4,6-tetra-O-acetyl-β-D-mannopyranosyl)-(1→4)-1,2,3,6-tetra-O-acetyl-α- and β-D-mannopyranoside (4)

2.26 g of galactomannan (2) soluble in 70% EtOH obtained above was dissolved in 23 ml of pyridine, 23 ml of acetic anhydride was added in the solution with cooling in an ice bath and stirred at 10° C. for 22 hours. To the reaction mixture was added ice water and extracted with chloroform, washed with water, aq. solution of $NaHCO_3$ and aq. solution of NaCl successively, and dried over anhydrous $MgSO_4$. After $MgSO_4$ was removed by Celite-filtration, the filtrate was concentrated in vacuo and the resulting residue was purified with silica-gel column chromatography (elution: toluene/ethyl acetate=2/1) to give 450 mg of the desired product (4).

Sample; a mixture of α:β=2:1; [α]D-0.5 (c 0.012, chloroform); $^1$H NMR δ ($CDCl_3$) 1.99~2.19 (all s, 24H, $8COCH_3$), 3.64 (m, 1H, H-5'), 3.77 (m, ⅓H, H-5β), 3.95~4.13 (m, 2+⅔H, H-5α, H-4β, H-4α and H-6'b), 4.23~4.37 (m, 3H, H-6bβ, H-6aα, H-6bα, H-6a' and H-6aβ), 4.72 (d, ⅓H, $J^β_{1',2}$= 1.1 Hz, H-1β'), 4.75 (d, ⅔H, $J^α_{1',2}$=1.1 Hz, H-1α'), 5.04 (m, 1H, H-3'), 5.17~5.25 (m, 2H, H-4', H-2α and H-3β), 5.39~5.45 (m, 2H, H-2', H-2β and H-3α), 5.81 (d, ⅓H, $J^β_{1,2}$= 1.1 Hz, H-1β), 6.03 (d, ⅔H, $J^α_{1,2}$=2.0 Hz, H-1α). Analysis calculated for $C_{28}H_{38}O_{19}$: C, 49.56; H, 5.64; Found: C, 49.34; H, 5.67. HR-FAB MS[M+Na]$^+$ Calculated for $C_{28}H_{38}O_{19}Na$: 701.191; Found 709.190. t.l.c; Rf=0.30 (toluene/ethyl acetate=1:1)

1.2. Hydrolysis of Guar Gum (A Large Scale)

(A)' Galactomannan Soluble in 70% EtOH is Obtained by Hydrolysis of Guar Gum with TFA 200 g of guar gum (1) was dissolved in 1660 ml of 1N TFA and heated to 110° C. in an oily bath with mechanical stirring for 35 min. When the guar gum was suspended, the mixture was sonicated for 15 min and mechanically stirred at 110° C. for 80 min. The reaction mixture was cooled with an ice bath, poured into 4 liter of 99% EtOH and placed at room temperature. The resulting white precipitation was removed by filtration using Buchner funnel and the filtrate was concentrated in vacuo. Toluene was added to the residue and azeotropically distilled several times to give 200.3 g of galactomannan (2) soluble in 70% EtOH and 9.9 g of galactomannan (3) insoluble in 70% EtOH. Analysis of galactomannan (2) soluble in 70% EtOH using MALDI-TOFMS showed that its polymerization degree was reduced to 1-8.

(B)' Galactomannan Soluble in 70% EtOH is Acetylated to Give O-(2,3,4,6-tetra-O-acetyl-β-D-mannopyranosyl)-(1→4)-1,2,3,6-tetra-O-acetyl-α- and β-D-mannopyranoside (4)

200.3 g of galactomannan (2) soluble in 70% EtOH obtained above was dissolved in 2100 ml of pyridine, 2100 ml of acetic anhydride was added in the solution with cooling in an ice bath and stirred at 10° C. for 22 hours. To the reaction mixture was added ice water and extracted with chloroform, washed with water, aq. solution of $NaHCO_3$ and aq. solution of NaCl successively, and dried over anhydrous $MgSO_4$. After $MgSO_4$ was removed by Celite-filtration, the filtrate was concentrated in vacuo and the resulting residue was partially purified with silica-gel column chromatography (elution: toluene/ethyl acetate=1/2), and then purified with the column chromatography of medium pressure (elution: toluene/ethyl acetate=2/1) to give 25.2 g of the desired product (4).

2. Synthesis of O-(2,3,4,6-tetra-O-acetyl-β-D-mannopyranosyl)-(1→4)-1,3,6-tri-O-acetyl-2-azide-2-deoxy-α-D-glucopyranoside (8)

Synthetic Scheme (2)

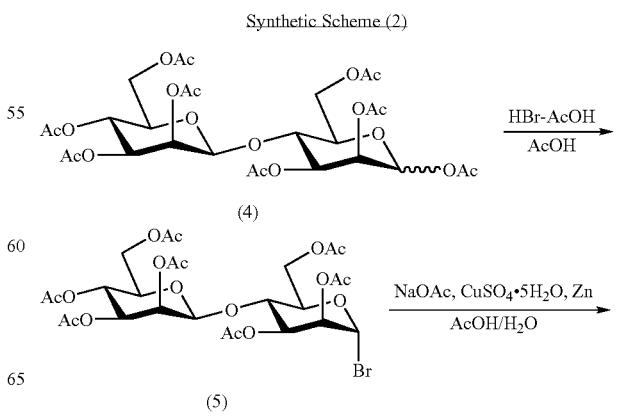

-continued

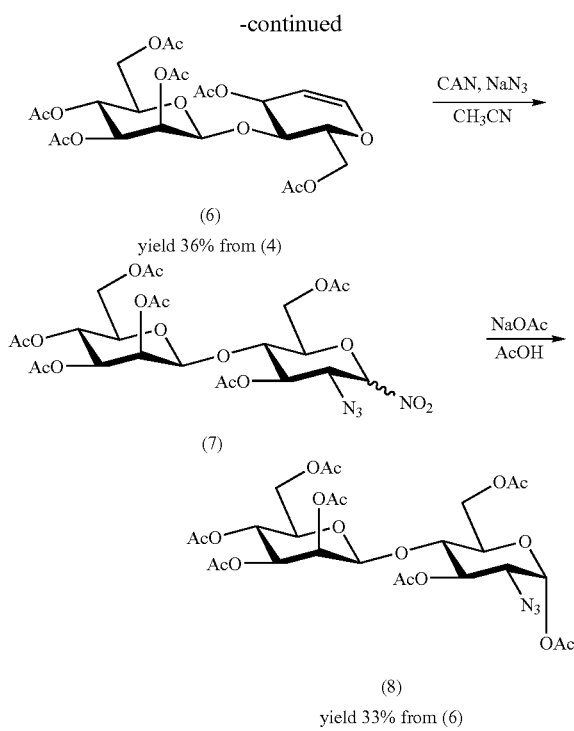

(6) yield 36% from (4)

(7)

(8) yield 33% from (6)

(C) Synthesis of O-(2,3,4,6-tetra-O-acetyl-β-D-mannopyranosyl)-(1→4)-2,3,6-tri-O-acetyl-α-D-mannopyranosyl bromide (5)

2.20 g of the compound (4) was dissolved in 19 ml of acetic acid, and to the solution was added 4.6 ml of 30% HBr—AcOH and the mixture was stirred at r.t. for 150 min in a dark place. After termination of the reaction was confirmed on t.l.c., ice water was added to the reaction mixture and the product was extracted with chloroform, washed with water, aq. solution of NaHCO₃ and aq. solution of NaCl successively, and dried over anhydrous MgSO₄. After Mg SO₄ was removed by celite-filtration, the filtrate was concentrated in vacuo to give 2.21 g of the residual mixture containing the desired product (5).

t.l.c.; Rf=0.35 (toluene/AcOEt=1:1)

(D) Synthesis of O-(2,3,4,6-tetra-O-acetyl-β-D-mannopyranosyl)-(1→4)-3,6-di-O-acetyl-D-glycol (6)

Into a three-neck flask cooled in ice water bath, were added 3.8 ml of acetic acid, 7.6 ml of water, 2.06 g of sodium acetate, 0.20 g of cupper sulfate pentahydrates and 1.65 g of zinc successively while being stirred with a mechanistic stirrer. Next, the reaction mixture containing the compound (5) was dissolved in 7.6 ml of acetic acid, and it was added to the reaction mixture above cooled in an ice water bath and the mixture was stirred at r.t. for 4 hours in a dark place. After termination of the reaction was confirmed on t.l.c., zinc was removed from the reaction mixture by celite-filtration and ice water was added to the filtrate. The product was extracted with chloroform, washed with water, aq. solution of NaHCO₃ and aq. solution of NaCl successively, and dried over anhydrous MgSO₄. After MgSO₄ was removed by celite-filtration and the filtrate was concentrated in vacuo. The residue was purified with a flash silica gel chromatography (elution: toluene/ethyl acetate=2/1) to give 0.64 g of the desired product (6).

Yield from the compound (4): 36%. $^1$H NMR δ(CDCl₃) 200, 2.05, 2.08, 2.10, 2.12 and 2.17 (all s, 18H, 6COCH₃), 3.66(ddd, 1H, $J_{4',5'}$=9.8 Hz, $J_{5',6a'}$=5.8 Hz, $J_{5',6b'}$=12.2 Hz, H-5'), 4.05(dd, 1H, $J_{3,4}$=6.0 Hz, $J_{4,5}$=8.1 Hz, H-4), 4.12(dd, 1H, $J_{5',6b'}$=2.6 Hz, $J_{6a',6b'}$=12.2 Hz, H-6b'), 4.13-4.17(m, 1H, H-5), 4.23(dd, 1H, $J_{5,6b}$=5.3 Hz, $J_{6a,6b}$=12.2 Hz, H-6b), 4.30 (dd, 1H, $J_{5',6a'}$=5.8 Hz, $J_{6a',6b'}$=12.2 Hz, H-6a'), 4.42(dd, 1H, $J_{5,6a}$=2.9 Hz, $J_{6a,6b}$=12.2 Hz, H-6a), 4.79(dd, 1H, $J_{1,2}$=6.1 Hz, $J_{2,3}$=3.1 Hz, H-2), 4.86(d, 1H, $J_{1',2'}$=1.1 Hz, H-1'), 5.05 (dd, 1H, $J_{2',3'}$=3.4 Hz, $J_{3',4'}$=10.1 Hz, H-3'), 5.22 (t, 1H, $J_{4',5'}$=9.8 Hz, H-4'), 5.45 (dd, 1H, $J_{1',2'}$=1.1 Hz $J_{2',3'}$=3.4 Hz, H-2'), 5.51 (m, 1H, H-3), 6.40 (dd, 1H, $J_{1,2}$=6.1 Hz, $J_{duble\ bond\ cis}$= 1.2 Hz, H-1) $^{13}$C NMR δ(CDCl₃) 20.5-21.0(m, 6COCH₃), 61.8(C-6), 62.5(C-6'), 65.9(C-4'), 68.5 (C-3 and C-2'), 70.8(C-3'), 72.6(C-5'), 74.0(C-4), 74.4(C-5), 97.9(C-1'), 99.0(C-2), 145.6(C-1), 169.5-170.6(m, 6COCH₃) t.l.c.; Rf=0.40 (toluene/ethyl acetate=1:1)

(E) Synthesis of O-(2,3,4,6-tetra-O-acetyl-β-D-mannopyranosyl)-(1→4)-3,6-di-O-acetyl-2-azide-2-deoxy α- and β-D-glucopyranosyl nitrate (7)

510 mg of the compound (6) was dissolved in 5.4 ml of anhydrous acetonitrile and stirred at −20° C. To the solution, 89 mg of sodium azide (NaN₃) was added, and then 1.50 g of cerium (IV) diammonium nitrate was added in four portions every 15 minutes. The reaction mixture was stirred under helium atmosphere at −20° C. for 18 hours. After termination of the reaction was confirmed on t.l.c., ice water was added to the reaction mixture and the product was extracted with chloroform, washed with water, aq. solution of NaHCO₃ and aq. solution of NaCl successively, and dried over anhydrous MgSO₄. After MgSO₄ was removed by celite-filtration, the filtrate was concentrated in vacuo to give 460 mg of the residue containing the desired product (7).

t.l.c.; Rf=0.50 (toluene/AcOEt=1:1)

(F) Synthesis of O-(2,3,4,6-tetra-O-acetyl-β-D-mannopyranosyl)-(1→4)-1,3,6-tri-O-acetyl-2-azide-2-deoxy-α-D-glucopyranoside (8)

460 mg of the residue containing the compound (7) was dissolved in 2.0 ml of acetic acid, and to the solution was added 170 mg of sodium acetate and stirred in an oil bath at 80° C. for 75 minutes. After termination of the reaction was confirmed on t.l.c., ice water was added to the reaction mixture and the product was extracted with chloroform, washed with water, aq. solution of NaHCO₃ and aq. solution of NaCl successively, and dried over anhydrous MgSO₄. After MgSO₄ was removed by celite-filtration and the filtrate was concentrated in vacuo. The residue was purified with a flash silica gel chromatography (elution: toluene/ethyl acetate=3/2) to give 360 mg of the residue containing the desired product (8) and O-(2,3,4,6-tetra-O-acetyl-β-D-mannopyranosyl)-(1→4)-1,3,6-tri-O-acetyl-2-azide-2-deoxy-α-D-mannopyranoside (9). The mixture was dissolved in a small amount of EtOH with heating, and then cooled in ice water to give a crystalline. Thus, 201 mg of the desired product was obtained.

t.l.c.; Rf=0.39 (toluene/AcOEt=1:1) Yield from the compound (6): 33%. $^1$H NMR δ(CDCl₃) 1.99, 2.05, 2.10, 2.12, 2.17 and 2.20 (all s, 21H, 7COCH$_3$), 3.51 (dd, 1H, J$_{1,2}$=3.8 Hz J$_{2,3}$=10.5 Hz, H-2), 3.61 (ddd,1H, J$_{4',5'}$=9.9Hz, J$_{5',6a'}$=5.0 Hz, J$_{5',6b'}$=2.8 Hz, H-5'), 3.83 (t, 1H, J$_{4,5}$=10.2 Hz, H-4), 3.99 (m, 1H, H-5), 4.12 (dd, 1H, J$_{5',6b'}$=2.8 Hz J$_{6a',6b'}$=12.3 Hz, H-6b'), 4.24 (dd, 1H, J$_{5,6b}$=3.7 Hz J$_{6a,6b}$=12.5 Hz, H-6b), 4.30(dd, 1H, J$_{5,6a}$=2.8 Hz, J$_{6a,6b}$=12.5 Hz, H-6a) 4.38(dd, 1H, J$_{5,6a}$=2.8Hz, J$_{6a,6b}$=12.5Hz, H-6a), 4.66 (d, 1H, J$_{1',2'}$=0.6 Hz, H-1'), 5.03 (dd, 1H, J$_{2',3'}$=3.2 Hz, J$_{3',4'}$=9.9 Hz, H-3'), 5.23 (t, 1H, J$_{4',5'}$=9.9 Hz, H-4'), 5.42 (dd, 1H, J$_{1',2'}$=0.6 Hz, J$_{2',3'}$=3.2 Hz, H-2'), 5.43 (dd, 1H, J$_{2,3}$=10.5 Hz, J$_{3,4}$=9.3 Hz, H-3), 6.24 (d, 1H, J$_{1,2}$=3.8 Hz, H-1) $^{13}$C NMR δ(CDCl$_3$) 20.5-20.9(m, 6COCH$_3$), 60.3(C-2), 61.9(C-6), 62.2(C-6'), 65.8(C-4'), 68.1 (C-2'), 69.7(C-3), 70.4(C-5), 70.7(C-3'), 72.5(C-5') 74.0(C-4), 89.9(C-1), 97.5(C-1'), 168.6-170.4(m, 6COCH$_3$) Analysis calculated for C$_{26}$H$_{35}$O$_{17}$: C, 47.20; H, 5.33; N, 6.35; Found: C, 46.90; H, 5.32; N, 6.39. HR-FAB MS[M+H]$^+$ Calculated for C$_{26}$H$_{36}$N$_3$O$_{17}$ 662.205, Found 662.202 mp+183.5–184.0° C. (from EtOH), t.l.c.; Rf=0.39 (toluene/ethyl acetate=1:1)

3. Synthesis of allyl O-(2,3,4,6-tetra-O-acetyl-β-D-mannopyranosyl)-(1→4)-O-(3,6-di-O-acetyl-2-azide-2-deoxy-β-D-glucopyranosyl)-(1→4)-3,6-di-O-benzyl-2-deoxy-2-phthalimide-β-D-glucopyranoside (13)

Synthetic scheme (3)

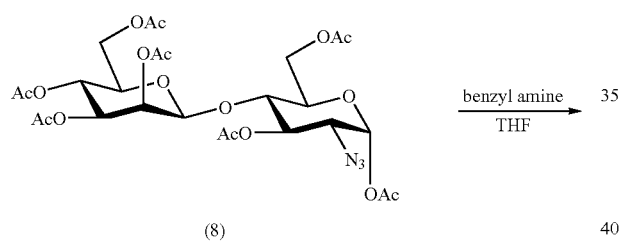

(8)

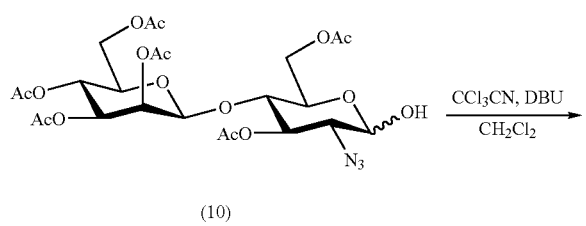

(10)
yield 92% from (8)

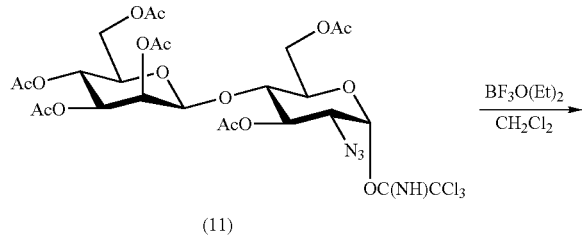

(11)
yield 76% from (10)

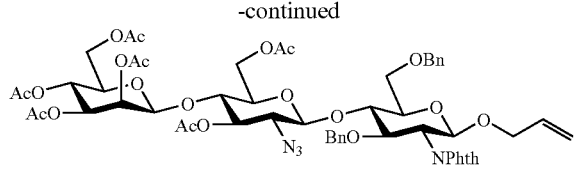

(13)
yield 30% from (11)

(G) synthesis of O-(2,3,4,6-tetra-O-acetyl-β-D-mannopyranosyl)-(1→4)-3,6-di-O-acetyl-2-azide-2-deoxy-D-glucopyranose (10)

300 mg of the compound (8) was dissolved in 3.0 ml of THF, and to the solution cooled in ice water was added 89 μl of benzylamine and stirred at r.t. for 48 hours. After termination of the reaction was confirmed on t.l.c., ice water was added to the reaction mixture and the product was extracted with chloroform, washed with water, 1N HCl and aq. solution of NaCl successively, and dried over anhydrous MgSO$_4$. After MgSO$_4$ was removed by celite-filtration and the filtrate was concentrated in vacuo. The residue was purified with a flash silica gel chromatography (elution: toluene/ethyl acetate=3/2) to give 257 mg of the desired product (10).

Yield from the compound (8): 92%. HR-FAB MS[M+H]$^+$ Calculated for C$_{24}$H$_{34}$N$_3$O$_{16}$ 620.194; Found 620.192. t.l.c; Rf=0.26 (toluene/AcOEt=1:1)

(H) Synthesis of O-(2,3,4,6-tetra-O-acetyl-β-D-mannopyranosyl)-(1→4)-3,6-di-O-acetyl-2-azide-2-deoxy-α-D-glucopyranosil trichloroacetoimidate (11)

85 mg of the compound (10) was dissolved in CH$_2$Cl$_2$ (550 μl) and CCl$_3$CN (275 μl), and to the solution cooled in ice water was added 10.2 μl of DBU and stirred at r.t. for 2 hours. After termination of the reaction was confirmed on t.l.c., the reaction mixture was concentrated in vacuo. The resulting residue was purified with a flash silica gel chromatography (elution: toluene/ethyl acetate=3/2) to give 80 mg of the desired product (11).

Yield from the compound (10): 76%. $^1$H NMR δ(CDCl$_3$) 1.97, 2.02, 2.07, 2.08, 2.16 and 2.17 (all s, 18H, 6COCH$_3$), 3.56-3.60(m, 1H, H-5'), 3.60(dd, 1H, J$_{1,2}$=3.4 Hz, J$_{2,3}$=10.5 Hz, H-2), 3.88(t, 1H, J$_{4,5}$=9.8 Hz, H-4), 4.09(dd, 1H, J$_{5',6b'}$=2.7 Hz, J$_{6a',6b'}$=12.5 Hz, H-6b'), 4.09-4.14(m, 1H, H-5), 4.21 (dd, 1H, J$_{5,6b}$=3.9 Hz, J$_{6a,6b}$=12.5 Hz, H-6b), 4.33(dd, 1H, J$_{5,6a}$=2.2 Hz, J$_{6a,6b}$=12.5 Hz, H-6a), 4.33(dd, 1H, J$_{5',6a'}$=4.9 Hz, J$_{6a',6b'}$=12.5 Hz, H-6a'), 4.69(s, 1H, H-1'), 5.01(dd, 1H, J$_{2',3'}$=3.4 Hz, J$_{3',4'}$=10.0 Hz, H-3'), 5.20(t, 1H, J$_{4',5'}$=9.8 Hz, H-4'), 5.38(d, 1H, J$_{2',3'}$=3.4 Hz, H-2'), 5.51(dd, 1H, J$_{2,3}$= 10.5 Hz, J$_{3,4}$=9.5 Hz, H-3), 6.41(d, 1H, J$_{1,2}$=3.4 Hz, H-1), 8.79(s, 1H, NH) $^{13}$C NMR δ(CDCl$_3$) 20.5-20.7(m, 6COCH$_3$), 60.8 (C-2), 61.9(C-6), 62.3(C-6'), 65.8(C-4'), 68.2(C-2'), 69.3(C-3), 70.7(C-5 and C-3'), 72.6(C-5'), 74.1(C-4), 90.5(C(NH) CCl$_3$), 94.1(C-1), 97.3(C-1'), 160.6(C(NH)CCl$_3$), 169.5-170.4(m, 6COCH$_3$) t.l.c; Rf=0.37 (toluene/ethyl acetate=1:1)

(I) Synthesis of allyl O-(2,3,4,6-tetra-O-acetyl-β-D-mannopyranosyl)-(1→4)-O-(3,6-di-O-acetyl-2-azide-2-deoxy-β-D-glucopyranosyl)-(1→4)-3,6-di-O-benzyl-2-deoxy-2-phthalimide-β-D-glucopyranoside (13)

47 mg of the compound (11) and 45 mg of allyl-O-3,6-O-di-benzyl-2-deoxy-2-phthalimide-β-D-glucopyranoside (12) were dissolved in 700 μl of $CH_2Cl_2$, and to the solution was added 70 mg of MS4A (Molecular Sieves) and stirred under nitrogen atmosphere at −20° C. for 30 minutes.

Next, 2.3 μl of $BF_3OEt_2$ was added and the mixture was stirred under nitrogen atmosphere at −20° C. for 24 hours. After termination of the reaction was confirmed on t.l.c., the reaction mixture was neutralized by adding triethylamine (TEA), MS4A was removed by celite filtration and the filtrate was concentrated in vacuo. The resulting residue was partially purified with a flash silica gel chromatography (elution: toluene/ethyl acetate=5/2) to give 32 mg of the residual mixture containing the desired compound (13) and allyl O-(2,3,4,6-tetra-O-acetyl-α-D-mannopyranosyl)-(1→4)-O-(3,6-di-O-acetyl-2-azide-2-deoxy-α-D-glucopyranosyl)-(1→4)-3,6-di-O-benzyl-2-deoxy-2-phthalimide-β-D-glucopyranoside (α:β=1:2). Furthermore, it was purified with HPLC (elution: hexane/ethanol=12/1) to give 21 mg of the desired product (13).

Yield from the compound (11): 31% $^1$H NMR δ($CDCl_3$) 1.90, 1.92, 1.96, 2.00, 2.07, 2.15 (all s, 18H, $6COCH_3$), 3.08 (m, 1H, H-5'), 3.27(dd, 1H, $J_{1',2'}$=8.1 Hz, $J_{2',3'}$=10.2 Hz, H-2'), 3.46(ddd, 1H, $J_{4'',5''}$=9.9 Hz, $J_{5'',6a''}$=4.8 Hz, $J_{5'',6b''}$=2.6 Hz, H-5''), 3.51-3.56(m, 1H, H-5), 3.56(t, 1H, $J_{4',5'}$=9.8 Hz, H-4'), 3.76(dd, 1H, $J_{5,6b}$=1.4 Hz, $J_{6a,6b}$=10.9 Hz, H-6b), 3.87(dd, 1H, $J_{5,6a}$=2.9 Hz, $J_{6a,6b}$=10.9 Hz, H-6a), 3.91(dd, 1H, J=6.3 Hz, J=13.0 Hz, CHH'CH=CH2), 3.98-4.20(m, 7H, H-6b'', H-6b', H-4, H-2, H-6a', H-3, CHH'CH=CH2), 4.27(dd, 1H, $J_{5'',6a''}$=4.8 Hz, $J_{6a'',6b''}$=12.3 Hz, H-6a''), 4.27 and 4.66(ABq, 2H, J=12.5 Hz, $PhCH_2$), 4.30(d, 1H, $J_{1',2'}$=8.1 Hz, H-1'), 4.42 and 4.73(ABq, 2H, J=12.0 Hz, $PhCH_2$), 4.45(s, 1H, H-1''), 4.76(dd, 1H, $J_{2',3'}$=3.4 Hz, $J_{3',4'}$=9.9 Hz, H-3'), 4.92(dd, 1H, $J_{2'',3''}$=3.4 Hz, $J_{3'',4''}$=9.9 Hz, H-3''), 4.93(dd, 1H, J=1.5 Hz, $J_{trans}$=10.4 Hz, CH=$CH_{trans}$H), 4.93(dd, 1H, J=1.5 Hz, $J_{cis}$=17.2 Hz, CH=CHcis), 5.06(d, 1H, $J_{1,2}$=8.4 Hz, H-1), 5.14(t, 1H, $J_{4'',5''}$=9.9 Hz, H-4''), 5.30(d, 1H, $J_{2'',3''}$=3.4 Hz, H-2''), 5.60(m, 1H, CH=CH2), 6.70-7.58(m, 14H, Ar—H) $^{13}$C NMR δ ($CDCl_3$) 20.5-20.6(m, $6COCH3$), 55.5(C-2), 62.2(C-6' and C-6''), 64.5(C-2'), 65.9(C-4''), 67.8(C-6), 68.1(C-2''), 69.7($CH_2CH=CH_2$), 70.7(C-3''), 71.9(C-3'), 72.0(C-5'), 72.5(C-5''), 73.5 and 74.3(2PhCH2), 74.6(C'-4 and C-5), 78.2(C-4), 97.3(C-1 and C-1''), 100.8(C-1'), 117.3 ($CH_2CH=CH_2$), 127.0-133.7(m, 18Ar—C), 137.9 ($CH_2CH=CH_2$), 169.6-170.4(m, 8C=O) HR-FAB MS[M+Na]$^+$ Calculated for $C_{55}H_{62}N_4O_{22}Na$, 1153.375, Found 1153.374 t.l.c; Rf=0.53 (toluene/ethyl acetate=1:1)

(J) (Data of Glycosyl Acceptor) allyl-O-3,6-di-O-benzyl-2-deoxy-2-phthalimide-β-D-glucopyranoside (12)

Amino-protected glucopyranoside (12) was synthesized according to the synthetic scheme shown below.

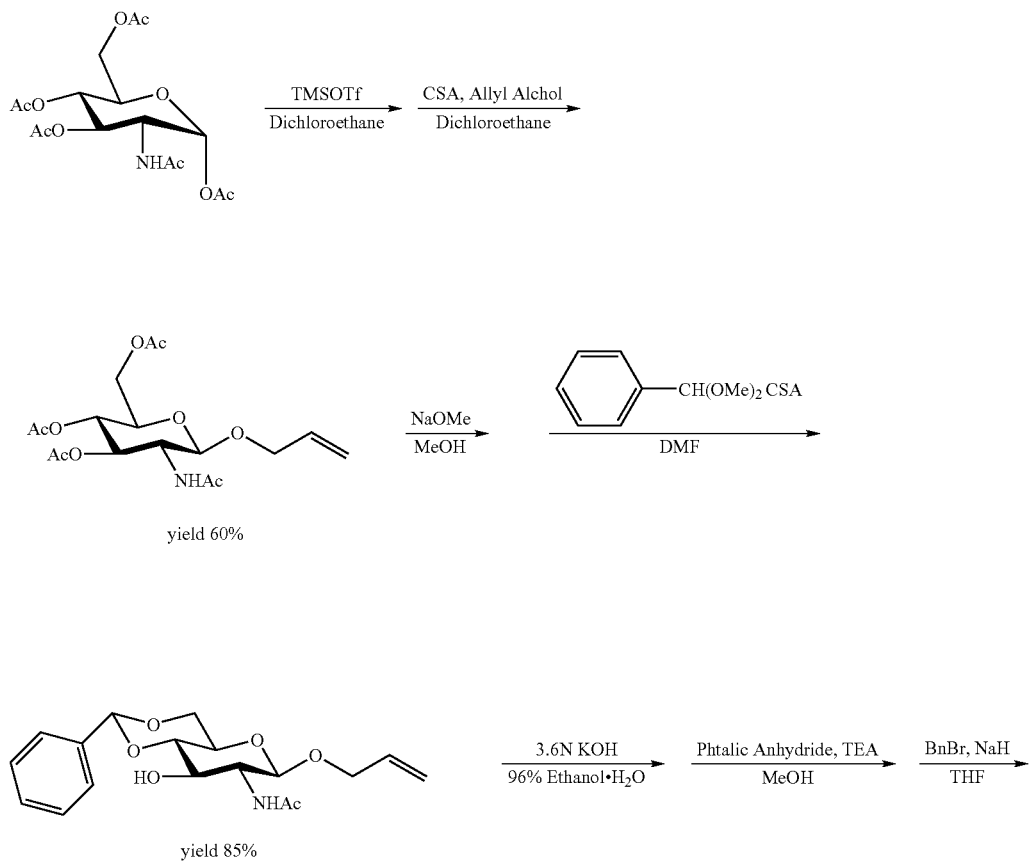

yield 60% yield 85%

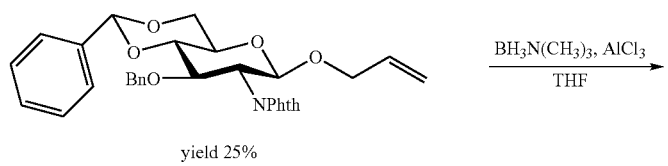 → 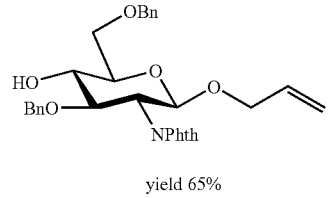

yield 25%    yield 65%

$^1$H NMR δ(CDCl$_3$) 3.63(m, 1H, H-5), 3.76-3.85(m, 3H, H-4, H-6a and H-6b), 3.97(dd, 1H, J=13.1 Hz, J=6.1 Hz, CHH'CH=CH$_2$), 4.15-4.26(m, 3H, H-2, H-3 and CHH'CH=CH$_2$), 4.52 and 4.73(ABq, 2H, J=12.2 Hz, PhCH2), 4.58 and 4.64(ABq, 2H, J=11.9 Hz, PhCH2), 4.99 (dd, 1H, J=1.3 Hz, J$_{trans}$=10.3 Hz, CH=CHcisH$_{trans}$), 5.07 (dd, 1H, J=1.3 Hz, J$_{cis}$=17.2 Hz, CH=CH$_{cis}$Htrans), 5.17(d, 1H, J$_{1,2}$=8.1 Hz, H-1), 5.61-5.70(m, 1H, CH=CH$_2$), 6.93-7.67(m, 14H, Ar—H) $^{13}$C NMR δ(CDCl$_3$) 55.3(C-2), 69.7 (C—C=C), 70.7(C-6), 73.5(C-5), 73.8 and 74.3(Ph-C), 74.5 (C-4), 78.7(C-3), 97.4(C-1), 117.3(C—C=C), 127.4-128.5 (m, Ar—C), 133.6(C—C=C), 137.6 and 138.2(C=O) HR-FAB MS[M+H]$^+$ Calculated for C$_{31}$H$_{32}$NO$_7$ 530.218, Found 530.215 t.l.c; Rf=0.72 (toluene/ethyl acetate=1:1)

INDUSTRIAL APPLICABILITY

Glycosyltransferase and an additive sugar unit are usually utilized in the automatic synthesizer of sugar chains since glycosyltransferase is convenient when a sugar chain is extended by adding a new saccharide. However, no glycosyltransferase is found to prepare the trisaccharide moiety (Manβ1→4GlcNβ1→4GlcN) of the reducing terminal in the core sugar chain structure of asparagine-linked glycoprotein and the chemical synthesis is the sole method for preparing it.

The present invention provides a convenient method for preparing the trisaccharide moiety of the reducing terminal in the core sugar chain utilizing galactomannan, guar gum and/or mannan derivatives, which are natural polysaccharides easily available at a reasonable cost.

The invention claimed is:
1. A method for preparing a trisaccharide (Manβ1→4GlcNβ1→4GlcN) of a reducing terminal in the core sugar chain structure of an asparagine-linked glycoprotein, comprising
(1) a process of preparing a mannose disaccharide compound (a type of ManP$^1$β1→4ManP$^1$) of the formula (I)

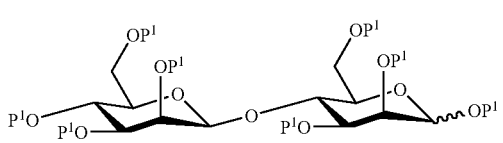

(I)

wherein P$^1$, OH-protecting group selected from the group consisting of acetyl, benzyl, 4-methoxybenzyl, benzoyl, methoxymethyl, tetrahydropyranyl, trimethylsilyl and triethylsilyl, and the wavy line means that —OP$^1$ is linked at an axial or equatorial position, or mixture of both, by hydrolyzing a polysaccharide having mannoseβ-1,4-bonds and protecting OH groups of the resulting hydrolysate, (2) a process of preparing a glycal compound, in which mannose of a reducing terminal of the mannose disaccharide is converted to glycal, by halogenation and reduction of the mannose disaccharide (a type of ManP$^1$β1→4ManP$^1$), (3) a process of preparing an azide disaccharide compound (a type of ManP$^1$β1→4ManP$^1$) shown with formula (II) in which a 2-azide group of mannose in a reducing terminal is linked at an equatorial position;

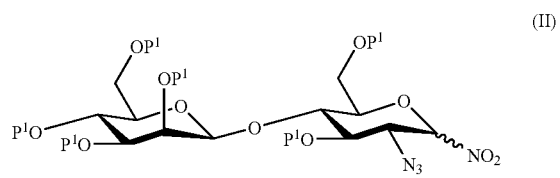

(II)

wherein P$^1$ is the same as described above, the wavy line means that —ONO$_2$ is linked at an axial or equatorial position, or mixture of both,
by azidenitration reaction of the glycal compound above, (4) a process of substituting the nitro group of the azide disaccharide compound (a type of ManP$^1$β1→4ManP$^1$) with a leaving group selected from the group consisting of fluorine atom, chlorine atom, trihaloacetoimidate, 4-pentenyl, alkylthio and arylthio, and (5) a process of preparing a trisaccharide compound (a type of Manβ1→4GlcNP$^1$β1→4GlcNP$^2$) shown with the formula (III);

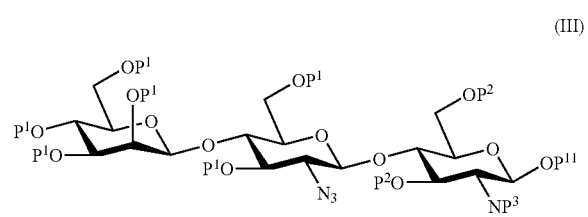

(III)

wherein P$^1$ is an OH-protecting group, as described above, P$^2$ is an OH-protecting group selected from the group consisting of acetyl, benzyl, 4-methoxybenzyl, benzoyl, methoxymethyl, tetrahydropyranyl, trimethylsilyl and triethylsilyl, P$^3$ is an amino-protecting group selected from the group consisting of phthalimide, tert-butyloxycarbonyl, benzyloxycarbonyl, acetyl, benzoyl and benzyl, and P$^{11}$ is an OH-protecting group selected from the group consisting of acetyl, benzyl, 4-methoxybenzyl, benzoyl, methoxymethyl, tetrahydropyranyl, trimethylsilyl and triethylsilyl,
by a reaction of the product having the leaving group with amino-protected glucopyranoside shown with the formula;

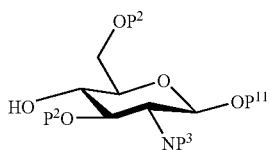

wherein P², P³ and P¹¹ are the same as described above.

2. The method for preparing a trisaccharide (Manβ1→4GlcNβ1→4GlcN) of a reducing terminal in a core sugar chain structure of an asparagine-linked glycoprotein of claim 1, further comprising
  (6) a process of preparing an asparagine-linked trisaccharide (Manβ1→4GlcNP¹β1→4GlcNP²) compound shown with the formula (IV);

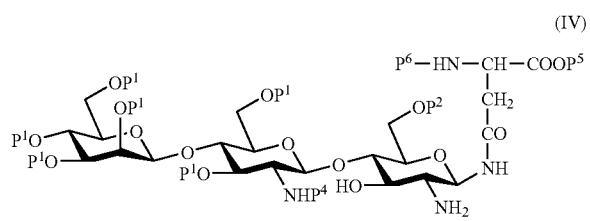

wherein P¹ and P² are independently OH-protecting groups, as described above, P⁴ and P⁶ are independently amino-protecting groups selected from the group consisting of phthalimide, tert-butyloxycarbonyl, benzyloxycarbonyl, acetyl, benzoyl and benzyl, and P⁵ is a carboxyl-protecting group which is t-Bu,
by deprotecting the P¹¹ group of the compound (III),

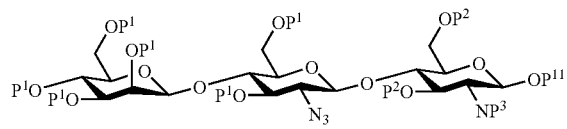

wherein P¹, P² and P¹¹ are independently OH-protecting groups, as described above, and P³ is an amino-protecting group, as described above,
reducing the azide group to an amino group, protecting the amino group with an acetyl group, forming an oxazoline ring simultaneously with deprotecting a hydroxy group of a reducing terminal, and coupling with a protected aspartic acid derivative of the formula:

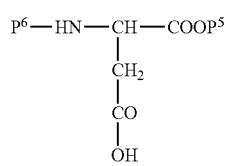

wherein P⁵ and P⁶ are the same as described above,
after introducing a —N=C=S group at the reducing terminal.

3. A method for preparing the azide disaccharide (a type of ManP¹β1→4ManP¹) shown with the formula (II) in which the 2-azide group of mannose in a reducing terminal is linked at the equatorial position;

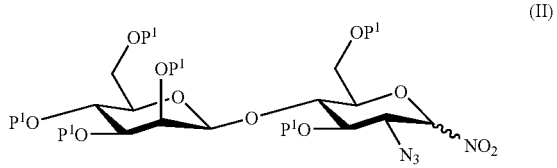

wherein P¹ is an OH-protecting group selected from the group consisting of acetyl, benzyl, 4-methoxybenzyl, benzoyl, methoxymethyl, tetrahydropyranyl, trimethylsilyl and triethylsilyl, and the wavy line means that —ONO₂ is linked at an axial or equatorial position, or mixture of both, comprising a process of preparing a glycal compound, in which mannose of the reducing terminal of the mannose disaccharide is converted to glycal, by halogenation and reduction of the mannose disaccharide compound (a type of ManP¹β1→4ManP¹) shown with the formula (I);

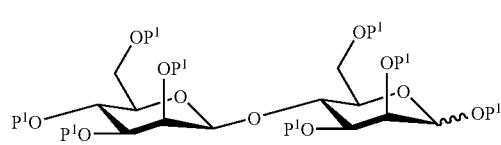

wherein P¹ is the same as described above and the wavy line means that —OP¹ is linked at an axial or equatorial position, or mixture of both,
and subsequent azidenitration reaction of the glycal compound.

4. A method for preparing the trisaccharide compound shown with the formula (III);

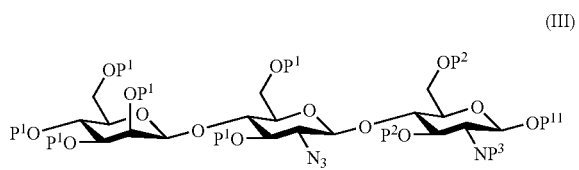

wherein P¹, P², and P¹¹ are independently OH-protecting groups selected from the group consisting of acetyl, benzyl, 4-methoxybenzyl, benzoyl, methoxymethyl, tetrahydropyranyl, trimethylsilyl and triethylsilyl, and P³ is an amino-protecting group selected from the group consisting of phthalimide, tert-butyloxycarbonyl, benzyloxycarbonyl, acetyl, benzoyl and benzyl, comprising a process of substituting the nitro group of the azide disaccharide compound (a type of ManP¹β1→4ManP¹) shown with the formula (II) with a leaving group selected from the group consisting of fluorine atom, chlorine atom, trihaloacetoimidate, 4-pentenyl, alkylthio and arylthio;

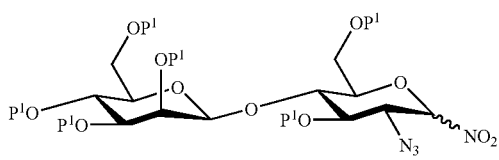

(II)

wherein P¹ is the same as described above, the wavy line means that —ONO₂ is linked at an axial or equatorial position, or mixture of both, and a 2-azide group of mannose in the reducing terminal is linked at the equatorial position, and next, reacting the substituted compound having the leaving group with amino-protected glucopyranoside of the formula;

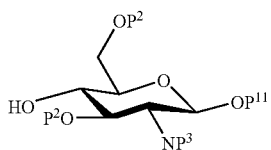

wherein P², P³ and P¹¹ are the same as described above.

5. A method for preparing an asparagine-linked trisaccharide compound (Manβ1→4GlcNP¹β1→4GlcNP²) shown with the formula (IV)

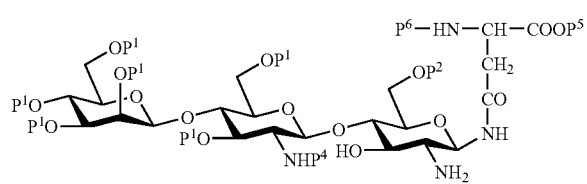

(IV)

wherein P¹ and P² are independently OH-protecting groups selected from the group consisting of acetyl, benzyl, 4-methoxybenzyl, benzoyl, methoxymethyl, tetrahydropyranyl, trimethylsilyl and triethylsilyl, P⁴ and P⁶ are independently amino-protecting groups selected from the group consisting of phthalimide, tert-butyloxycarbonyl, benzyloxycarbonyl, acetyl, benzoyl and benzyl, and P⁵ is a carboxyl-protecting group which is t-Bu, by deprotecting the P¹¹ group of the compound (III),

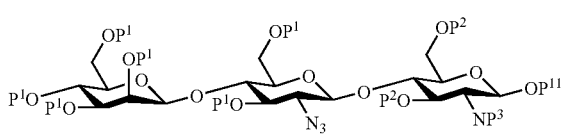

(III)

wherein P¹ and P² are the same as described above, P³ is an amino-protecting group selected from the group consisting of phthalimide, tert-butyloxycarbonyl, benzyloxycarbonyl, acetyl, benzoyl and benzyl, and P¹¹ is an OH-protecting group selected from the group consisting of acetyl, benzyl, 4-methoxybenzyl, benzoyl, methoxymethyl, tetrahydropyranyl, trimethylsilyl and triethylsilyl, reducing the azide group to an amino group, protecting the amino group with an acetyl group, forming an oxazoline ring simultaneously with deprotecting a hydroxy group of a reducing terminal, and coupling with a protected aspartic acid derivative of the formula:

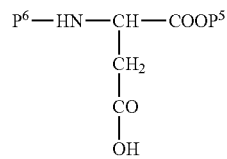

wherein P⁵ and P⁶ are the same as described above, after introducing a —N=C=S group at the reducing terminal.

6. The azide disaccharide (a type of ManP¹β1→4ManP¹) compound shown with the formula (II);

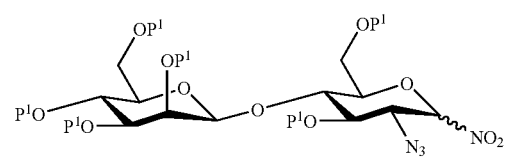

(II)

wherein P¹ is an OH-protecting group selected from the group consisting of acetyl, benzyl, 4-methoxybenzyl, benzoyl, methoxymethyl, tetrahydropyranyl, trimethylsilyl and triethylsilyl, and the wavy line means that —ONO₂ is linked at an axial or equatorial position, or mixture of both.

7. A trisaccharide compound (a type of Manβ1→4GlcNP¹β1→4GlcNP²) shown with the formula of (III);

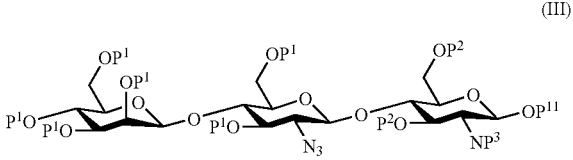

(III)

wherein P¹, P² and P¹¹ are independently OH-protecting groups selected from the group consisting of acetyl, benzyl, 4-methoxybenzyl, benzoyl, methoxymethyl, tetrahydropyranyl, trimethylsilyl and triethylsilyl, and P³ is an amino-protecting group selected from the group consisting of phthalimide, tert-butyloxycarbonyl, benzyloxycarbonyl, acetyl, benzoyl and benzyl.

8. A method for preparing a trisaccharide (Manβ1→4GlcNβ1→4GlcN) of a reducing terminal in a core sugar chain structure of an asparagine-linked glycoprotein, comprising (1) a process of preparing a mannose disaccharide compound (a type of ManP$^1$β1→4ManP$^1$) of the formula (I)

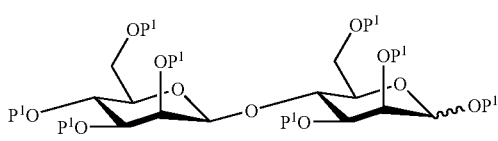

wherein P$^1$ is an OH-protecting group selected from the group consisting of acetyl, benzyl, 4-methoxybenzyl, benzoyl, methoxymethyl, tetrahydropyranyl, trimethylsilyl and triethylsilyl, and the wavy line means that —OP$^1$ is linked at an axial or equatorial position, or mixture of both, by hydrolyzing guar gum or galactomannan of the formula (V);

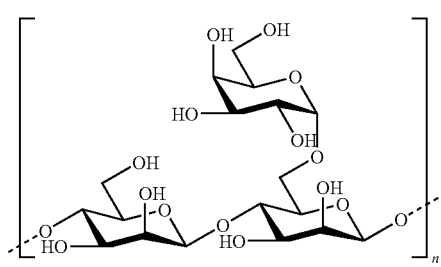

wherein n is an integer of 50 or more,
and protecting OH groups of the resulting hydrolysate.

(2) a process of preparing a glycal compound, in which mannose of a reducing terminal of the mannose disaccharide is converted to glycal, by halogenation and reduction of the mannose disaccharide (a type of ManP$^1$β1→4ManP$^1$), and (3) a process of preparing an azide disaccharide compound (a type of ManP$^1$β1→4ManP$^1$) shown with formula (II) in which a 2-azide group of mannose in a reducing terminal is linked at an equatorial position;

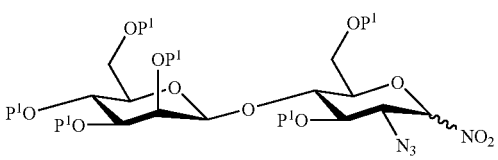

wherein P$^1$ is the same as described above, the wavy line means that —ONO$_2$ is linked at an axial or equatorial position, or mixture of both,
by azidenitration reaction of the glycal compound above, (4) a process of substituting the nitro group of the azide disaccharide compound (a type of ManP$^1$β1→4ManP$^1$) with a leaving group selected from the group consisting of fluorine atom, chlorine atom, trihaloacetoimidate, 4-pentenyl, alkylthio and arylthio, and (5) a process of preparing a trisaccharide compound (a type of Manβ1→4GlcNP$^1$β1→4GlcNP$^2$) shown with the formula (III);

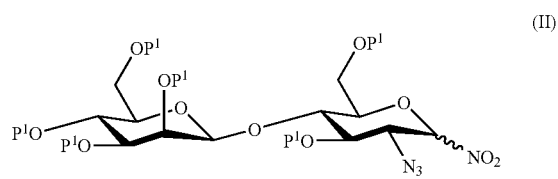

wherein P$^1$ an OH-protecting group, as described above, P$^2$ is an OH-protecting group selected from the group consisting of acetyl, benzyl, 4-methoxybenzyl, benzoyl, methoxymethyl, tetrahydropyranyl, trimethylsilyl and triethylsilyl, P$^3$ is an amino-protecting group selected from the group consisting of phthalimide, tert-butyloxycarbonyl, benzyloxycarbonyl, acetyl, benzoyl and benzyl, and P$^{11}$ is an OH-protecting group selected from the group consisting of acetyl, benzyl, 4-methoxybenzyl, benzoyl, methoxymethyl, tetrahydropyranyl, trimethylsilyl and triethylsilyl, by a reaction of the product having the leaving group with amino-protected glucopyranoside shown with the formula;

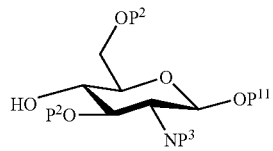

wherein P$^2$, P$^3$, and P$^{11}$ are the same as described above.

9. The method for preparing a trisaccharide (Manβ1→4GlcNβ1→4GlcN) of a reducing terminal in a core sugar chain structure of an asparagine-linked glycoprotein of claim 8, further comprising (6) a process of preparing an asparagine-linked trisaccharide (Manβ1→4GlcNP$^1$β1→4GlcNP$^2$) compound shown with the formula (IV);

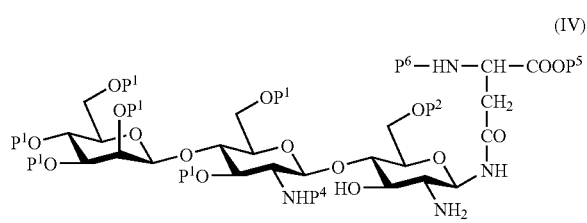

wherein P$^1$ and P$^2$ are independently OH-protecting groups, as described above, P$^4$ and P$^6$ are independently amino-protecting groups selected from the group consisting of phthalimide, tert-butyloxycarbonyl, benzyloxycarbonyl, acetyl, benzoyl and benzyl, and $P^5$ is a carboxyl-protecting group which is t-Bu,
by deprotecting the $P^{11}$ group of the compound (III),

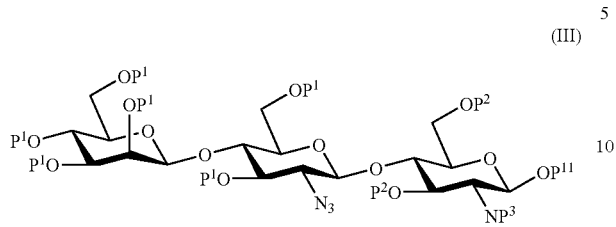

(III)

wherein $P^1$, $P^2$ and $P^{11}$ are independently OH-protecting groups, as described above, and $P^3$ is an amino-protecting group, as described above,
reducing the azide group to an amino group, protecting the amino group with an acetyl group, forming an oxazoline ring simultaneously with deprotecting a hydroxy group of a reducing terminal, and coupling with a protected aspartic acid derivative of the formula:

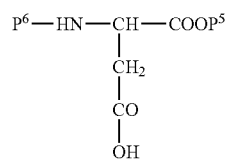

wherein $P^5$ and $P^6$ are the same as described above,
after introducing a —N=C=S group at the reducing terminal.

* * * * *

UNITED STATES PATENT AND TRADEMARK OFFICE
CERTIFICATE OF CORRECTION

PATENT NO. : 7,598,372 B2
APPLICATION NO. : 10/584065
DATED : October 6, 2009
INVENTOR(S) : Nishimura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 144 days.

Signed and Sealed this

Twenty-eighth Day of September, 2010

David J. Kappos
*Director of the United States Patent and Trademark Office*